(12) United States Patent
Muller et al.

(10) Patent No.: US 11,413,225 B2
(45) Date of Patent: *Aug. 16, 2022

(54) HAIR DYEING COMPOSITION COMPRISING AN OXIDATION DYE, A SCLEROGLUCAN GUM, AN ALCANOLAMINE AND A MINERAL ALKALINE AGENT

(71) Applicant: L'OREAL, Paris (FR)

(72) Inventors: Sabrina Muller, Saint-Ouen (FR); Delphine Charrier, Saint-Ouen (FR); Mladen Milic, Saint-Ouen (FR); Cindy Yadel, Saint-Ouen (FR); Fanny Cardonnel, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/252,974

(22) PCT Filed: Jun. 20, 2019

(86) PCT No.: PCT/EP2019/066369
§ 371 (c)(1),
(2) Date: Dec. 16, 2020

(87) PCT Pub. No.: WO2019/243512
PCT Pub. Date: Dec. 26, 2019

(65) Prior Publication Data
US 2021/0212909 A1 Jul. 15, 2021

(30) Foreign Application Priority Data
Jun. 20, 2018 (FR) ...................... 1855431

(51) Int. Cl.
*A61Q 5/10* (2006.01)
*A61K 8/22* (2006.01)
*A61K 8/04* (2006.01)
*A61K 8/34* (2006.01)
*A61K 8/41* (2006.01)
*A61K 8/60* (2006.01)
*A61K 8/67* (2006.01)
*A61K 8/73* (2006.01)
*A61K 8/81* (2006.01)

(52) U.S. Cl.
CPC .............. *A61K 8/22* (2013.01); *A61K 8/042* (2013.01); *A61K 8/345* (2013.01); *A61K 8/416* (2013.01); *A61K 8/60* (2013.01); *A61K 8/676* (2013.01); *A61K 8/731* (2013.01); *A61K 8/817* (2013.01); *A61Q 5/10* (2013.01); *A61K 2800/4324* (2013.01); *A61K 2800/48* (2013.01); *A61K 2800/594* (2013.01); *A61K 2800/596* (2013.01)

(58) Field of Classification Search
CPC . A61Q 5/10; A61K 8/22; A61K 8/411; A61K 8/4926; A61K 8/415; A61K 2800/4324; A61K 8/41; A61K 8/347; A61K 8/416; A61K 8/731; A61K 8/42; A61K 8/817; A61K 8/345; A61K 8/60; A61K 2800/48; A61K 2800/596
USPC .......................................................... 8/405
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |

(Continued)

FOREIGN PATENT DOCUMENTS

| | | |
|---|---|---|
| DE | 2359399 A1 | 6/1975 |
| DE | 3843892 A1 | 6/1990 |

(Continued)

OTHER PUBLICATIONS

International Search Report and Written Opinion for counterpart Application No. PCT/EP2019/066365, dated Aug. 13, 2019.

(Continued)

*Primary Examiner* — Eisa B Elhilo

(74) *Attorney, Agent, or Firm* — The Marbury Law Group, PLLC

(57) ABSTRACT

The disclosure relates to a composition for dyeing keratin fibers, in particular human keratin fibers such as hair, comprising one or more dyes, one or more scleroglucan gums in a total weight content greater than or equal to 0.5% relative to the total weight of the composition, one or more mineral alkaline agents, and one or more organic alkaline agents selected from the alkanolamines. The disclosure also relates to a method for dyeing keratin fibers using said composition and to a multi-compartment device suitable for implementing said composition.

20 Claims, No Drawings

(56) References Cited

U.S. PATENT DOCUMENTS

| | | |
|---|---|---|
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,240,450 A | 12/1980 | Grollier et al. |
| 4,349,532 A | 9/1982 | Vanlerberghe et al. |
| 4,381,919 A | 5/1983 | Jacquet et al. |
| 4,591,610 A | 5/1986 | Grollier |
| 4,702,906 A | 10/1987 | Jacquet et al. |
| 4,719,282 A | 1/1988 | Nadolsky et al. |
| 4,761,273 A | 8/1988 | Grollier et al. |
| 4,839,166 A | 6/1989 | Grollier et al. |
| 4,874,554 A | 10/1989 | Lange et al. |
| 4,996,059 A | 2/1991 | Grollier et al. |
| 5,061,289 A | 10/1991 | Clausen et al. |
| 5,089,252 A | 2/1992 | Grollier et al. |
| 5,180,397 A | 1/1993 | Grollier et al. |
| 5,180,399 A | 1/1993 | Grollier et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 6,099,592 A | 8/2000 | Vidal et al. |
| 2003/0229948 A1 | 12/2003 | Desenne et al. |
| 2004/0034946 A1 | 2/2004 | Legrand et al. |
| 2004/0060125 A1 | 4/2004 | Audouset |
| 2004/0064901 A1 | 4/2004 | Kleen et al. |
| 2004/0133993 A1 | 7/2004 | Cottard et al. |
| 2004/0172771 A1 | 9/2004 | Cottard et al. |
| 2004/0221401 A1 | 11/2004 | Desenne et al. |
| 2005/0039270 A1 | 2/2005 | Legrand et al. |
| 2006/0117493 A1 | 6/2006 | Bureiko et al. |
| 2006/0182697 A1 | 8/2006 | Lalleman et al. |
| 2008/0282481 A1 | 11/2008 | De Boni et al. |
| 2010/0175202 A1 | 7/2010 | Simonet et al. |
| 2010/0192969 A1* | 8/2010 | DeGeorge ............ A61K 8/23 132/208 |
| 2010/0199441 A1 | 8/2010 | Hercouet et al. |
| 2011/0117037 A1* | 5/2011 | Legrand ............ A61Q 5/065 424/62 |
| 2011/0150797 A1 | 6/2011 | Legrand et al. |
| 2011/0203605 A1 | 8/2011 | Allard et al. |
| 2011/0203606 A1 | 8/2011 | Recchion et al. |
| 2011/0209720 A1 | 9/2011 | DeGeorge et al. |
| 2012/0076930 A1 | 3/2012 | Miller |
| 2012/0210523 A1 | 8/2012 | Lalleman et al. |
| 2013/0042883 A1 | 2/2013 | DeGeorge et al. |
| 2013/0167862 A1 | 7/2013 | Lopez et al. |
| 2014/0082855 A1 | 3/2014 | Rapold et al. |
| 2014/0305464 A1 | 10/2014 | DeGeorge et al. |
| 2014/0326270 A1 | 11/2014 | DeGeorge et al. |
| 2015/0143637 A1 | 5/2015 | Rapold et al. |
| 2015/0335545 A1 | 11/2015 | Rapold et al. |
| 2016/0279036 A1 | 9/2016 | Schoepgens et al. |
| 2017/0172901 A1 | 6/2017 | Kerl et al. |
| 2017/0354584 A1* | 12/2017 | Lalleman ............ A61K 8/347 |

FOREIGN PATENT DOCUMENTS

| | | |
|---|---|---|
| DE | 4133957 A1 | 4/1993 |
| DE | 19543988 A1 | 5/1997 |
| EP | 0080976 A1 | 6/1983 |
| EP | 0122324 A1 | 10/1984 |
| EP | 0337354 A1 | 10/1989 |
| EP | 0770375 A1 | 5/1997 |
| FR | 1492597 A | 8/1967 |
| FR | 1583363 A | 10/1969 |
| FR | 2077143 A5 | 10/1971 |
| FR | 2080759 A1 | 11/1971 |
| FR | 2162025 A | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| FR | 2618070 A1 | 1/1989 |
| FR | 2633940 A1 | 7/1991 |
| FR | 2733749 A1 | 11/1996 |
| FR | 2801308 A1 | 5/2001 |
| FR | 2886136 A1 | 12/2006 |
| FR | 3008615 A1 | 1/2015 |
| GB | 1026978 A | 4/1966 |
| GB | 1153196 A | 5/1969 |
| GB | 1546809 A | 5/1979 |
| GB | 2207443 A | 2/1989 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 2016/091816 A1 | 6/2016 |
| WO | 2018/056235 A1 | 3/2018 |
| WO | 2019/243505 A1 | 12/2019 |
| WO | 2019/243507 A1 | 12/2019 |
| WO | 2019/243508 A1 | 12/2019 |
| WO | 2019/243509 A1 | 12/2019 |
| WO | 2019/243511 A1 | 12/2019 |
| WO | 2019/243513 A1 | 12/2019 |

OTHER PUBLICATIONS

International Search Report and Written Opinion for counterpart Application No. PCT/EP2019/066368, dated Sep. 3, 2019.
International Search Report and Written Opinion for counterpart Application No. PCT/EP2019/066363, dated Sep. 2, 2019,.
International Search Report and Written Opinion for counterpart Application No. PCT/EP2019/066369, dated Aug. 22, 2019.
International Search Report and Written Opinion for counterpart Application No. PCT/EP2019/066364, dated Sep. 11, 2019.
International Search Report and Written Opinion for counterpart Application No. PCT/EP2019/066361, dated Aug. 22, 2019.
International Search Report and Written Opinion for counterpart Application No. PCT/EP2019/066370, dated Sep. 11, 2019.
Mintel, "Root Vanish," Kazumi, ID 3319563, XP055562798, dated Feb. 27, 2015.
Mintel, "Colourant Cream," LG Household and Health Care, ID 1533817, , XP055547325, dated May 11, 2011.
Mintel, "Hair Colourant," Garnier, ID 644332, XP055547333, dated Jan. 16, 2007.
Non-Final Office Action for copending U.S. Appl. No. 17/252,856, dated Aug. 16, 2021.
Non-Final Office Action for copending U.S. Appl. No. 17/252,883, dated Aug. 18, 2021.
Non-Final Office Action for copending U.S. Appl. No. 17/253,035, dated Aug. 20, 2021.
Non-Final Office Action for copending U.S. Appl. No. 17/253,007, dated Aug. 25, 2021.
Non-Final Office Action for copending U.S. Appl. No. 17/252,870, dated Sep. 10, 2021.

(56) References Cited

OTHER PUBLICATIONS

Non-Final Office Action for copending U.S. Appl. No. 17/253,019, dated Sep. 24, 2021.
Final Office Action for copending U.S. Appl. No. 17/253,019, dated Feb. 22, 2022.

* cited by examiner

HAIR DYEING COMPOSITION COMPRISING AN OXIDATION DYE, A SCLEROGLUCAN GUM, AN ALCANOLAMINE AND A MINERAL ALKALINE AGENT

CROSS REFERENCE TO RELATED APPLICATION

This is a national stage application of PCT/EP2019/066369, filed internationally on Jun. 20, 2019, which claims priority to French Application No. 1855431, filed on Jun. 20, 2018, both of which are incorporated by reference herein in their entireties. The present invention relates to a composition for dyeing keratin fibers, in particular human keratin fibers such as the hair, comprising one or more oxidation dyes, one or more scleroglucan gums in a total weight content of greater than or equal to 0.5% relative to the total weight of the composition; one or more mineral alkaline agents and one or more organic alkaline agents chosen from mineral alkanolamine(s).

The invention also relates to a dyeing process involving the application of said composition to keratin fibers, in particular human keratin fibers such as the hair, and also to a multi-compartment device that is suitable for implementing said dye composition.

The present invention relates to the field of dyeing keratin fibers and more particularly to the field of hair dyeing.

Among the methods for dyeing human keratin fibers, such as the hair, mention may be made of oxidation dyeing or permanent dyeing. More particularly, this form of dyeing uses one or more oxidation dyes, usually one or more oxidation bases optionally combined with one or more couplers.

The variety of molecules used as oxidation bases and couplers allows a wide range of colors to be obtained.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloring, via an oxidative condensation reaction between the oxidation dyes.

Oxidation dyeing must moreover satisfy a certain number of requirements. Thus, it must be free of toxicological drawbacks, it must enable shades to be obtained in the desired intensity and it must show a good wear property in the face of external attacking factors such as light, bad weather, washing, permanent waving, perspiration and rubbing.

The dyeing process must also make it possible to cover gray hair and, finally, must be as unselective as possible, i.e. it must make it possible to produce the smallest possible color differences along the same keratin fiber, which generally includes areas that are differently sensitized (i.e. damaged) from its end to its root, so as to obtain the most uniform possible coloring of the keratin fibers. Dye compositions must also make it possible to give good cosmetic properties to keratin fibers, in particular care, softness and/or hold, and must have good working qualities, in particular they must be easy to apply, while at the same time achieving visible (i.e. notably intense, chromatic), uniform and fast coloring results.

The compositions used in a dyeing process must also have good mixing and application properties on keratin fibers, and notably good rheological properties so as not to run down the face, onto the scalp or beyond the areas that it is proposed to dye, when they are applied; this notably allows uniform application from the roots to the ends.

The composition according to the invention also shows very good stability over time for several weeks.

In particular, it is sought to obtain dye compositions that are stable over time for several weeks. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage.

Specifically, it is desirable for the dye compositions to be stable over time, in particular stable after 1 month at 45° C., or even after 2 months at 45° C.

It is also sought to obtain dye compositions that are stable over a wide pH range and in particular with respect to extreme pH values, for example to alkaline pH values ranging from 9 to 12. Finally, the dye compositions may occasionally be destabilized (undergo phase separation) by high contents of certain compounds, for instance of oxidation dyes and/or cationic compounds such as cationic polymers, and it is thus desirable for these compositions to be stable under these conditions, in particular for them not to undergo phase separation.

These aims and others are achieved by the present invention, one subject of which is thus a composition (A) for dyeing keratin fibers, preferably human keratin fibers such as the hair, comprising:
- one or more oxidation dyes;
- one or more scleroglucan gums in a total content of greater than or equal to 0.5% by weight relative to the weight of the composition;
- one or more mineral alkaline agents; and
- one or more alkaline agents chosen from alkanolamine(s).

Another subject of the invention relates to a ready-to-use composition for dyeing keratin fibers, in particular human keratin fibers such as the hair, obtained after mixing a composition (A) comprising:
- one or more oxidation dyes;
- one or more scleroglucan gums in a total amount of greater than or equal to 0.5% by weight relative to the weight of the composition;
- one or more mineral alkaline agents; and
- one or more organic alkaline agents chosen from alkanolamine(s);
- and a composition (B) comprising one or more chemical oxidizing agents.

For the purposes of the invention, the term "ready-to-use composition" refers to any composition that is intended to be applied immediately to keratin fibers.

The invention is also directed toward a process for dyeing keratin fibers, and in particular human keratin fibers such as the hair, involving the application to the fibers of a dye composition as defined previously, and of an oxidizing composition (B) comprising at least one chemical oxidizing agent, preferably chosen from hydrogen peroxide and/or one or more systems for generating hydrogen peroxide, preferably from hydrogen peroxide, the oxidizing composition (B) being mixed with the dye composition just before use (application to said fibers) (extemporaneously) or at the time of use, or alternatively the dye composition and oxidizing composition being applied sequentially without intermediate rinsing.

A subject of the invention is also a multi-compartment device (or "kit") allowing the implementation of the composition for dyeing keratin fibers, preferably comprising at least two compartments, a first compartment containing the dye composition (A) as defined previously, and the second compartment containing at least one oxidizing composition (B) comprising at least one chemical oxidizing agent, preferably chosen from hydrogen peroxide and/or one or more systems for generating hydrogen peroxide, preferably from hydrogen peroxide, the compositions in the compartments being intended to be mixed before application, to give the formulation after mixing; in particular, the kit may be an aerosol device.

For the purposes of the present invention, the term "composition for dyeing" or "dye composition" means a composition intended to be applied to keratin fibers, preferably human keratin fibers and in particular the hair, optionally after mixing with an oxidizing composition comprising at least one chemical oxidizing agent. For the purposes of the present invention, the term "ready-to-use dye composition" or "ready-to-use composition" means a composition resulting from mixing a dye composition and an oxidizing composition. The ready-to-use dye composition may be prepared just before application to said keratin fibers.

The compositions according to the invention thus make it possible to give very good dyeing performance on keratin fibers, notably in terms of build-up, intensity, chromaticity and/or selectivity. They also afford compositions which have good rheological properties so as not to run down onto the face, the scalp or beyond the areas that it is proposed to dye, when they are applied.

The compositions according to the invention are stable. For the purposes of the present invention, the term "stable" in particular means that physical properties such as the appearance, the pH and/or the viscosity vary little or not at all over time, and in particular that the viscosity of the composition does not change or changes little during storage and/or that the composition does not undergo phase separation during storage. In particular, it is desirable for the dye compositions to be stable over time, in particular stable after 1 month at 45° C., or even after 2 months at 45° C.

Furthermore, the compositions according to the invention have the advantage of being stable (of not undergoing phase separation) independently of the pH and in particular with respect to extreme pH values, especially to alkaline pH values of greater than or equal to 9, for example to alkaline pH values ranging from 9 to 12. Finally, the compositions are preferably stable (do not undergo phase separation) even in the presence of a high content of certain compounds, for instance of oxidation dyes and/or cationic compounds such as cationic polymers.

Moreover, the compositions of the invention are advantageously translucent, which gives them a visual appearance that the consumer finds esthetic and attractive.

In particular, the compositions according to the invention afford very good dyeing properties while at the same time reducing the unpleasant odors when compared with conventional dye compositions.

Other features and advantages of the invention will emerge more clearly on reading the description and the examples that follow.

In the text hereinbelow, unless otherwise indicated, the limits of a range of values are included in that range, notably in the expressions "between" and "ranging from . . . to . . . ".

The keratin fibers are preferably human keratin fibers, preferably the hair.

The expression "at least one" is equivalent to the expression "one or more".

Advantageously, the composition according to the invention has a thickened texture, in cream or gel form, preferably in gel form, preferably it is translucent.

Thus, the composition according to the invention generally has, at room temperature (25° C.), a viscosity of greater than 50 cps, preferably between 200 and 100 000 cps, more preferentially between 500 and 50 000 cps, even more preferentially between 800 and 10 000 cps, and better still from 1000 to 8000 cps measured at 25° C. at a spin speed of 200 rpm using a rheometer such as a Rheomat RM 180 equipped with a No. 3 or 4 spindle, the measurement preferably being taken after 60 seconds of rotation of the spindle (after which time stabilization of the viscosity and of the spin speed of the spindle is observed).

Oxidation Dyes

Composition (A) according to the invention comprises one or more oxidation dyes.

The oxidation dye precursors that may be used in the present invention are generally chosen from oxidation bases, optionally combined with one or more couplers.

The oxidation bases may preferably be chosen from para-phenylenediamines, bis(phenyl)alkylenediamines, para-aminophenols, ortho-aminophenols and heterocyclic bases, and the addition salts thereof.

Preferentially, the oxidation base(s) of the invention are chosen from para-phenylenediamines and heterocyclic bases. Among the para-phenylenediamines, examples that may be mentioned include para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(o-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, 2-methoxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and 2-methoxymethyl-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(o-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol, and the addition salts thereof.

Among the heterocyclic bases, it is possible in particular pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino 3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308.

Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and also the addition salts thereof.

More particularly, the oxidation bases according to the invention are chosen from 3-aminopyrazolo[1,5-a]pyridines preferably substituted in position 2 with:

a) a (di)($C_1$-$C_6$)(alkyl)amino group, the alkyl groups possibly being substituted with one or more hydroxyl, amino or imidazolium groups;

b) a cationic or non-cationic 5- to 7-membered heterocycloalkyl group comprising from 1 to 3 heteroatoms, optionally substituted with one or more ($C_1$-$C_6$)alkyl groups such as di($C_1$-$C_4$)alkylpiperazinium;

c) a ($C_1$-$C_6$)alkoxy group optionally substituted with one or more hydroxyl groups, such as β-hydroxyalkoxy, and also the addition salts thereof.

Among the pyrimidine derivatives, mention may be made of the compounds described, for example, in patents DE 2359399, JP 88169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. Preferably, the heterocyclic oxidation bases of the invention are chosen from 4,5-diaminopyrazoles such as 4,5-diamino-1-(β-hydroxyethyl)pyrazole. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl) pyrazole and/or a salt thereof.

Pyrazole derivatives that may also be mentioned include diamino-N,N-dihydropyrazolopyrazolones and notably those described in patent application FR-A-2 886 136, such as the following compounds and the addition salts thereof. 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a] pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

As heterocyclic bases, use will preferentially be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The oxidation base(s) used in the context of the invention are generally present in an amount ranging from 0.001% to 10% by weight approximately, and preferably ranging from 0.005% to 5%, relative to the total weight of the dye composition.

The additional couplers that are conventionally used for the dyeing of keratin fibers are preferably chosen from meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2-methyl-5-aminophenol, 3-amino-2-chloro-6-methylphenol, 2-methyl-5-hydroxyethylaminophenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, thymol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are notably chosen from the addition salts with an acid, such as hydrochlorides, hydrobromides, sulfates, citrates, succinates, tartrates, lactates, tosylates, benzenesulfonates, phosphates and acetates.

In the context of the present invention, when they are present, the coupler(s) are generally present in a total amount ranging from 0.001% to 10% by weight approximately relative to the total weight of the dye composition, and preferably ranging from 0.005% to 5% by weight relative to the total weight of the dye composition.

Preferably, the total content of oxidation dyes in the composition according to the invention is between 0.001% and 20% by weight, preferably between 0.001% and 10% by weight, preferably between 0.01% and 5% by weight, relative to the weight of the composition.

According to a particular embodiment, the composition comprises at least one oxidation base and at least one coupler.

Scleroglucan Gums

According to the invention, composition (A) comprises one or more scleroglucan gums in a total content of greater than or equal to 0.5% by weight relative to the weight of the composition.

Scleroglucan gums are polysaccharides of microbial origin produced by a fungus of *Sclerotium* type, in particular *Sclerotium rolfsii*. They are polysaccharides constituted solely of glucose units.

Scleroglucan gums may or may not be modified. Preferably, the scleroglucan gums used in the present invention are unmodified.

Examples of scleroglucan gums that may be used in the present invention are, in a nonlimiting manner, the products sold under the name Actigum CS, in particular Actigum CS 11, by the company Sanofi Bio Industries and under the name Amigum or Amigel by the company Alban Miller International.

Other scleroglucan gums, such as the gum treated with glyoxal described in French patent application No. 2 633 940, may also be used.

The scleroglucan gum(s) that may be used according to the invention preferably represent a total content ranging from 0.5% to 10% by weight, more preferentially from 0.5% to 5% by weight, even more preferentially from 0.5% to 3% by weight, better still from 0.5% to 2% by weight and even more preferentially from 0.7% to 1.5% by weight, relative to the total weight of composition (A).

According to one embodiment of the invention, the oxidizing composition (B) comprises one or more scleroglucan gums, preferably in a total content of greater than or equal to 0.5% by weight relative to the weight of the composition.

Preferably, according to this embodiment, the scleroglucan gum(s) that may be used according to the invention preferably represent from 0.5% to 10% by weight, more preferentially from 0.5% to 5% by weight, even more preferentially from 0.5% to 3% by weight, even more preferentially and even more preferentially from 0.5% to 2%, even from 0.7% to 2% by weight, relative to the total weight of the oxidizing composition (B).

Alkaline Agents

The composition according to the invention comprises one or more mineral alkaline agents and one or more organic alkaline agents chosen from alkanolamine(s).

The "alkaline agents" may equivalently be referred to as "basifying agents".

The term "mineral alkaline agent" (also known as an inorganic alkaline agent) means an alkaline agent which is not organic.

The mineral alkaline agent(s) are preferably chosen from aqueous ammonia, also known as ammonium hydroxide (or ammonia precursors such as ammonium salts, for example ammonium halides and in particular ammonium chloride), alkali metal or alkaline-earth metal silicates, phosphates, carbonates or bicarbonates, such as alkali metal or alkaline-earth metal metasilicates, sodium or potassium carbonate or bicarbonate, sodium or potassium hydroxide, or mixtures thereof.

Preferably, the mineral alkaline agent(s) are chosen from aqueous ammonia (or ammonia precursors such as ammonium salts, for example ammonium halides and in particular ammonium chloride) and/or alkali metal or alkaline-earth metal metasilicates.

Preferably, the mineral alkaline agent(s) are present in a total content ranging from 0.1% to 10% by weight, more preferentially from 0.5% to 8% by weight and better still from 1% to 7% by weight, relative to the total weight of the composition.

When the composition comprises aqueous ammonia (ammonium hydroxide), its content preferably ranges from 0.1% to 10% by weight, more preferentially from 0.5% to 8% by weight and better still from 1% to 6% by weight, relative to the total weight of the composition.

The composition according to the invention also comprises one or more organic alkaline agents chosen from alkanolamines.

The term "alkanolamine" means an organic amine comprising a primary, secondary or tertiary amine function, and one or more linear or branched $C_1$ to $C_8$ alkyl groups bearing one or more hydroxyl radicals.

Preferably, the organic amines chosen from alkanolamines such as monoalkanolamines, dialkanolamines or trialkanolamines comprising one to three identical or different $C_1$ to $C_4$ hydroxyalkyl radicals.

Preferably, the alkanolamines are preferably chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane, and mixtures thereof, preferably monoethanolamine (MEA).

Preferably, the alkanolamine(s) is/are present in a total content preferably ranging from 0.5% to 10% by weight, more preferentially from 1% to 9% by weight, better still from 2% to 8% by weight relative to the total weight of the composition.

Preferably, the weight ratio of the total content of mineral alkaline agents relative to the total content of alkanolamines ranges from 0.05 to 10, more preferentially from 0.1 to 5 and better still from 0.15 to 3.

Particularly preferably, the composition according to the invention comprises aqueous ammonia (ammonium hydroxide) and one or more alkanolamines, preferably monoethanolamine.

Additional Alkaline Agents

The composition according to the invention may also comprise one or more additional alkaline agents other than mineral alkaline agents and alkanolamines.

Preferably, the additional alkaline agent(s) may be chosen from organic alkaline agents other than alkanolamines By way of example, mention may be made of amino acids.

By way of amino acids which can be used in the composition according to the present invention, mention may especially be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the additional alkaline agents are chosen from basic amino acids, notably comprising an additional amine function optionally included in a ring or in a ureido function.

Preferably, the additional alkaline agent(s) are chosen from amino acids, preferably basic amino acids, preferably arginine.

Preferably, when the composition according to the invention contains one or more additional alkaline agents other than mineral alkaline agents and alkanolamines, they are present in a total content ranging from 0.5% to 10% by weight, more preferentially from 1% to 8% by weight and better still from 2% to 7% by weight, relative to the total weight of the composition.

Associative Polymer

The composition according to the invention may also comprise one or more associative polymers. The associative polymers according to the invention are polymers comprising at least one $C_8$-$C_{30}$ fatty chain and of which the molecules are capable, in the formulation medium, of associating with each other or with molecules of other compounds.

Preferably, the fatty chain includes from 10 to 30 carbon atoms.

A particular case of associative polymers is amphiphilic polymers, i.e. polymers including one or more hydrophilic parts which make them water-soluble and one or more hydrophobic zones (comprising at least one fatty chain) via which the polymers interact and assemble with each other or with other molecules.

The associative polymers that may be used in the composition according to the invention may be chosen from nonionic, anionic, cationic and amphoteric associative polymers, and mixtures thereof.

According to one embodiment of the invention, the associative polymer(s) are chosen from nonionic associative polymers.

The nonionic associative polymers are preferably chosen from:

(1) celluloses modified with groups including at least one fatty chain;
   preferably from:
      hydroxyethylcelluloses modified with groups including at least one fatty chain, such as alkyl, arylalkyl or alkylaryl groups, or mixtures thereof, and in which the alkyl groups are preferably $C_5$-$C_{22}$, preferably such as the cetylhydroxyethylcellulose sold notably under the reference Natrosol Plus Grade 330 CS ($C_{16}$ alkyls) sold by the company Ashland, or the product Polysurf 67CS sold by the company Ashland,
      hydroxyethylcelluloses modified with polyalkylene glycol ether alkyl phenol groups, such as the product Amercell Polymer HM-1500 (polyethylene glycol (15) ether of nonyl phenol) sold by the company Amerchol,
   and mixtures thereof.

(2) hydroxypropyl guars modified with groups including at least one fatty chain, such as the product Esaflor HM 22 ($C_{22}$ alkyl chain) sold by the company Lamberti, and the products RE210-18 ($C_{14}$ alkyl chain) and RE205-1 ($C_2$ alkyl chain) sold by the company Rhodia.

(3) copolymers of vinylpyrrolidone and of fatty-chain hydrophobic monomers:
   mention may be made, by way of example, of:
      the products Antaron V216 or Ganex V216 (vinylpyrrolidone/hexadecene copolymer) sold by the company I.S.P.
      the products Antaron V220 or Ganex V220 (vinylpyrrolidone/eicosene copolymer) sold by the company I.S.P.

(4) copolymers of $C_1$-$C_6$-alkyl methacrylates or acrylates and of amphiphilic monomers comprising at least one fatty chain, for instance the oxyethylenated methyl acrylate/stearyl acrylate copolymer sold by the company Goldschmidt under the name Antil 208.

(5) copolymers of hydrophilic methacrylates or acrylates and of hydrophobic monomers comprising at least one fatty chain, for instance the polyethylene glycol methacrylate/lauryl methacrylate copolymer.

(6) polyurethane polyethers comprising in their chain both hydrophilic blocks usually of polyoxyethylenated nature and hydrophobic blocks, which may be aliphatic sequences alone and/or cycloaliphatic and/or aromatic sequences.

(7) polymers with an aminoplast ether backbone containing at least one fatty chain, such as the Pure Thix compounds sold by the company Sud-Chemie.

(8) and mixtures thereof.

Particularly preferably, the associative polymer(s) are nonionic associative polymer(s), and preferably chosen from celluloses modified with groups including at least one fatty chain.

Preferably, the nonionic associative polymer(s) are chosen from hydroxyethylcelluloses modified with groups including at least one fatty chain, such as alkyl, arylalkyl or alkylaryl groups, or mixtures thereof, and in which the alkyl groups are preferably $C_8$-$C_{22}$, and hydroxyethylcelluloses modified with polyalkylene glycol ether alkyl phenol groups, and mixtures thereof, preferably cetylhydroxyethylcellulose.

Cationic polymers According to an advantageous embodiment of the invention, the composition comprises one or more cationic polymers.

As cationic polymers that may be used in the compositions according to the invention, mention may be made in particular of:

(1) cyclopolymers of alkyldiallylamine or of dialkyldiallylammonium, such as the homopolymers or copolymers including, as main constituent of the chain, units corresponding to formula (I) or (II):

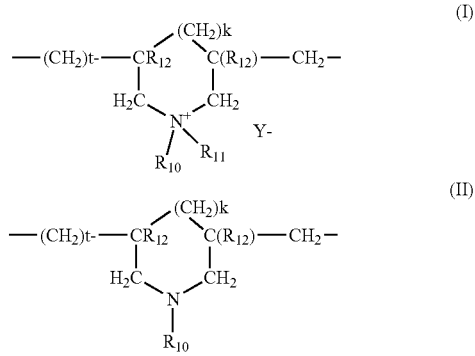

in which
k and t are equal to 0 or 1, the sum k+t being equal to 1;
$R12$ denotes a hydrogen atom or a methyl radical;
$R10$ and $R11$, independently of each other, denote a C1-C6 alkyl group, a C1-C5 hydroxyalkyl group, a C1-C4 amidoalkyl group; or alternatively $R10$ and $R11$ may denote, together with the nitrogen atom to which they are attached, a heterocyclic group such as piperidyl or morpholinyl; $R10$ and $R11$, independently of each other, preferably denote a C1-C4 alkyl group;
$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer, for example sold under the name Merquat 100 by the company Nalco. Preferably, the polymers of family (1) are chosen from dialkyldiallylammonium homopolymers.

(2) quaternary diammonium polymers comprising repeating units of formula:

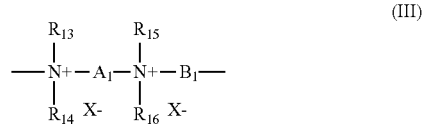

in which:
$R13$, $R14$, $R15$ and $R16$, which may be identical or different, represent aliphatic, alicyclic or arylaliphatic radicals comprising from 1 to 20 carbon atoms or $C_1$-$C_{12}$ hydroxyalkyl aliphatic radicals, or else $R13$, $R14$, $R15$ and $R16$, together or separately, form, with the nitrogen atoms to which they are attached, heterocycles optionally comprising a second non-nitrogen heteroatom;

or else $R13$, $R14$, $R15$ and $R16$ represent a linear or branched $C_1$-$C_6$ alkyl radical substituted with a nitrile, ester, acyl, amide or —CO—O—R17-D or —CO—NH—R17-D group, where $R17$ is an alkylene and D is a quaternary ammonium group;

$A1$ and $B1$ represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

it being understood that $A1$, $R13$ and $R15$ can form, with the two nitrogen atoms to which they are attached, a piperazine ring;

in addition, if $A1$ denotes a linear or branched, saturated or unsaturated alkylene or hydroxyalkylene radical, $B1$ may also denote a group (CH2)n-CO-D-OC—(CH2)p- with n and p, which may be identical or different, being integers ranging from 2 to 20, and D denoting:

a) a glycol residue of formula —O—Z—O—, in which Z denotes a linear or branched hydrocarbon-based radical or a group corresponding to one of the following formulae: —(CH2CH2O)x-CH2CH2- and —[CH2CH(CH3)O]y-CH2CH(CH3)-, in which x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula —NH—Y—NH—, in which Y denotes a linear or branched hydrocarbon-based radical, or else the divalent radical —CH2-CH2-S—S—CH2-CH2-;

d) a ureylene group of formula —NH—CO—NH—.

Preferably, X– is an anion, such as chloride or bromide. These polymers have a number-average molar mass (Mn) generally of between 1000 and 100 000.

Mention may be made more particularly of cationic polymers that are constituted of repeating units corresponding to the formula:

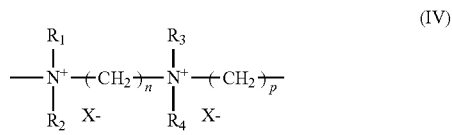

in which R1, R2, R3 and R4, which may be identical or different, denote an alkyl or hydroxyalkyl radical containing from 1 to 4 carbon atoms, n and p are integers ranging from 2 to 20, and X— is an anion derived from a mineral or organic acid.

A particularly preferred compound of formula (IV) is the one for which R1, R2, R3 and R4 represent a methyl radical and n=3, p=6 and X=Cl, known as Hexadimethrine chloride according to the INCI (CTFA) nomenclature.

Preferably, the cationic polymer(s) are chosen from dialkyldiallylammonium homopolymers, in particular homopolymers of dimethyldiallylammonium salts, polymers constituted of repeating units corresponding to formula (IV) above, in particular poly(dimethyliminio)-1,3-propanediyl (dimethyliminio)-1,6-hexanediyl dichloride, the INCI name of which is hexadimethrine chloride, and mixtures thereof.

When they are present, the total content of cationic polymers in the composition according to the present invention may range from 0.01% to 10% by weight relative to the weight of the composition, preferably from 0.1% to 7% relative to the weight of the composition, even more advantageously from 0.5% to 5% by weight and better still from 0.5% to 3% by weight relative to the weight of the composition.

Carboxylic Acids

The dye composition (A) according to the invention may advantageously comprise one or more carboxylic acids, and/or addition salts thereof and/or solvates thereof, said carboxylic acid(s) being aliphatic compounds, comprising from 2 to 10 carbon atoms and preferably comprising at least two carboxylic groups.

Preferably, they are chosen from aliphatic dicarboxylic and/or tricarboxylic acids comprising from 2 to 10 carbon atoms, preferably from 2 to 8 carbon atoms, better still from 2 to 6 carbon atoms.

Preferably, the carboxylic acids may be chosen from oxalic acid, malonic acid, malic acid, glutaric acid, citraconic acid, citric acid, maleic acid, succinic acid, adipic acid, tartaric acid, fumaric acid, and mixtures thereof.

Preferably, the carboxylic acid(s) comprise at least two carboxylic groups and are chosen from malonic acid, citric acid, maleic acid, glutaric acid, succinic acid, and mixtures thereof; preferably chosen from malonic acid, citric acid, maleic acid, and mixtures thereof.

More particularly preferably, the carboxylic acid is citric acid.

The total content of carboxylic acid(s) and/or addition salts thereof and/or solvates thereof preferably ranges from 0.1% to 20% by weight, relative to the total weight of composition (A).

Preferably, the total content of carboxylic acid(s) ranges from 0.1% to 20%, preferentially from 0.5% to 10% by weight, better still from 1% to 7% by weight, relative to the total weight of the composition, and even better still from 2% to 5% by weight relative to the total weight of composition (A).

Surfactants

Preferably, the composition according to the present invention also comprises one or more surfactants, which may be chosen from anionic surfactants, amphoteric or zwitterionic surfactants, nonionic surfactants and cationic surfactants, and mixtures thereof, preferably from nonionic surfactants, cationic surfactants, and mixtures thereof.

The term "anionic surfactant" means a surfactant including, as ionic or ionizable groups, only anionic groups. These anionic groups are preferably chosen from the following groups: $CO_2H$, $CO_2^-$, $S_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$-POH and $PO^-$.

According to one embodiment, the composition according to the invention comprises one or more nonionic surfactants.

The nonionic surfactants that may be used according to the invention may be chosen from:
alcohols, α-diols and ($C_1$-$C_{20}$)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain including from 8 to 40 carbon atoms and notably from 16 to 30 carbon atoms; in particular, oxyethylenated alcohols comprising at least one saturated or unsaturated, linear or branched $C_8$ to $C_{40}$ alkyl chain, comprising from 1 to 100 mol of ethylene oxide, preferably from 2 to 50 and more particularly from 2 to 40 mol of ethylene oxide and including one or two fatty chains;

condensates of ethylene oxide and propylene oxide with fatty alcohols;

polyethoxylated fatty amides preferably containing from 2 to 30 ethylene oxide units, polyglycerolated fatty amides including on average from 1 to 5 and in particular from 1.5 to 4 glycerol groups;

ethoxylated fatty acid esters of sorbitan, preferably containing from 2 to 40 ethylene oxide units;

fatty acid esters of sucrose;

polyoxyalkylenated, preferably polyoxyethylenated, fatty acid esters containing from 2 to 150 mol of ethylene oxide, including oxyethylenated plant oils;

N—($C_6$-$C_{24}$ alkyl)glucamine derivatives;

amine oxides such as ($C_{10}$-$C_{14}$ alkyl)amine oxides or N—($C_{10}$-$C_{14}$ acyl)aminopropylmorpholineoxides;

and mixtures thereof.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of $C_8$/$C_{16}$-alkyl (poly)glycosides 1,4, notably as an aqueous 53% solution, such as those sold by Cognis under the reference Plantacare® 818 UP.

Preferentially, the nonionic surfactants are chosen from:
saturated or unsaturated, linear or branched, oxyethylenated fatty alcohols including at least one $C_8$ to $C_{40}$, notably $C_5$-$C_{20}$ and better still $C_{10}$-$C_{18}$ alkyl chain, and comprising from 1 to 100 mol of ethylene oxide, preferably from 2 to 50, more particularly from 2 to 40 mol, or even from 3 to 20 mol of ethylene oxide; and ($C_6$-$C_{24}$ alkyl)(poly)glycosides, and more particularly ($C_8$-$C_{18}$ alkyl)(poly)glycosides;

and mixtures thereof;

and even more preferentially from ($C_6$-$C_{24}$ alkyl)(poly)glycosides, preferentially ($C_8$-$C_{18}$ alkyl)(poly)glycosides.

According to a preferred embodiment of the invention, the composition according to the invention comprises one or more nonionic surfactants preferably chosen from alkyl (poly)glycosides. Preferably, the composition according to the invention comprises one or more surfactants chosen from ($C_6$-$C_{24}$ alkyl)(poly)glycosides, more preferentially from ($C_8$-$C_{18}$ alkyl)(poly)glycosides, preferably from $C_8$/$C_{16}$-(poly)glucosides, preferably of 1,4 type, and preferably chosen from decyl glucosides and/or caprylyl/capryl glucosides and/or cocoyl glucosides.

According to a first embodiment, the surfactant(s) are nonionic, preferably chosen from ($C_6$-$C_{24}$ alkyl)polyglycosides.

According to a preferred embodiment, the composition according to the invention comprises at least one or more cationic surfactants. Preferably, the surfactant(s) are chosen from optionally polyoxyalkylentated primary, secondary or tertiary fatty amine salts, quaternary ammonium salts, and mixtures thereof.

Preferably, the cationic surfactant(s) are chosen from cetyltrimethylammonium, behenyltrimethylammoniumand-dipalmitoylethylhydroxyethylmethylammoniumsalts, and mixtures thereof, and more particularly behenyltrimethylammonium chloride, cetyltrimethylammonium chloride, and dipalmitoylethylhydroxyethylammonium methosulfate, and mixtures thereof.

The composition preferably comprises one or more cationic surfactants in a total content ranging from 0.01% to 20% by weight, more preferentially from 0.05% to 10% by weight and better still from 0.1% to 5% by weight, relative to the total weight of the composition.

The composition preferably comprises one or more nonionic surfactants in a total content ranging from 0.01% to 10% by weight, more preferentially from 0.05% to 5% by weight and better still from 0.1% to 3% by weight, relative to the total weight of the composition.

The composition preferably comprises one or more cationic surfactants in a total content ranging from 0.01% to 10% by weight, more preferentially from 0.05% to 5% by weight and better still from 0.1% to 3% by weight, relative to the total weight of the composition.

Preferably, the surfactant(s) are chosen from cationic or nonionic surfactants, and mixtures thereof, preferably cationic surfactants. Preferably, the composition according to the invention comprises at least one or more cationic surfactants and one or more nonionic surfactants.

Medium

The cosmetically acceptable medium that is suitable for dyeing keratin fibers, also known as a dye "support", generally comprises water or a mixture of water and of at least one organic solvent to dissolve the compounds that are not sufficiently water-soluble.

More particularly, the organic solvents are chosen from linear or branched and preferably saturated monoalcohols or diols, comprising from 2 to 10 carbon atoms, such as ethyl alcohol, isopropyl alcohol, hexylene glycol (2-methyl-2,4-pentanediol), neopentyl glycol and 3-methyl-1,5-pentanediol; glycerol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol monomethyl ether, butylene glycol or dipropylene glycol; and also diethylene glycol alkyl ethers, notably of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight, relative to the total weight of the composition.

The compositions used according to the invention generally comprise water or a mixture of water and of one or more organic solvents or a mixture of organic solvents.

The composition according to the invention preferably comprises water.

Preferably, the water content ranges from 5% to 95% by weight, more preferentially from 10% to 90% by weight and better still from 20% to 80% by weight, relative to the total weight of the composition.

pH of the Medium

The pH of the composition according to the invention generally ranges from 1 to 12. Preferably, the pH of composition (A) according to the invention is basic.

For the purposes of the present invention, the term "basic pH" means a pH above 7.

Preferably, the pH of composition (A) according to the invention is above 8, and particularly ranges from 8.5 to 12.

Preferably, the pH of the composition is between 9 and 12.

pH Adjuster

The cosmetically acceptable medium may be adjusted to the desired value by means of acidifying or basifying agents usually used in the dyeing of keratin fibers, or alternatively using standard buffer systems.

Among the acidifying agents, examples that may be mentioned include mineral acids, for instance hydrochloric acid, (ortho)phosphoric acid, boric acid, nitric acid or sulfuric acid, or organic acids, for instance compounds comprising at least one sulfonic acid function, a phosphonic acid function or a phosphoric acid function, or compounds bearing a carboxylic acid function such as those mentioned previously.

Other Additives

The composition according to the invention may also contain various additives conventionally used in hair dye compositions, such as mineral thickeners, and in particular fillers such as clays or talc; organic thickeners other than scleroglucan gums; antioxidants; penetrants; sequestrants; fragrances; dispersants; film-forming agents; ceramides; preserving agents; opacifiers; fatty substances and/or additional direct dyes.

The above additives are generally present in an amount for each of them of between 0.01% and 40% by weight relative to the weight of the composition, and preferably between 0.05% and 20% by weight relative to the weight of the composition.

Needless to say, a person skilled in the art will take care to select this or these additional compound(s) such that the advantageous properties intrinsically associated with the composition(s) that are useful in the dyeing process in accordance with the invention are not, or are not substantially, adversely affected by the envisioned addition(s).

Dyeing Process

Another subject of the invention is a dyeing process using a dye composition (A) as described previously, with an oxidizing composition (B) comprising one or more chemical oxidizing agents.

In particular, the invention is also directed toward a process for dyeing keratin fibers, and in particular human keratin fibers such as the hair, involving the application to the fibers of a dye composition (A) as defined previously, and of an oxidizing composition (B) comprising at least one chemical oxidizing agent, preferably chosen from hydrogen peroxide and/or one or more systems for generating hydrogen peroxide, preferably from hydrogen peroxide, the oxidizing composition (B) being mixed with the dye composition (A) just before use (i.e. application to said fibers) (extemporaneously) or at the time of use, or alternatively the dye composition and oxidizing composition being applied sequentially without intermediate rinsing.

Oxidizing Agent:

The oxidizing composition (B) used with the dye composition (A) according to the invention contains one or more chemical oxidizing agents, preferably chosen from hydrogen peroxide and/or one or more systems for generating hydrogen peroxide.

The term "chemical oxidizing agent" means an oxidizing agent other than atmospheric oxygen.

Preferably, the chemical oxidizing agent(s) are chosen from hydrogen peroxide, peroxygenated salts, for instance persulfates, perborates, peracids and precursors thereof, percarbonates of alkali metals or alkaline-earth metals, such as sodium carbonate peroxide, also known as sodium percarbonate and peracids and precursors thereof; alkali metal bromates or ferricyanides, solid hydrogen peroxide-generating chemical oxidizing agents such as urea peroxide and polymer complexes that can release hydrogen peroxide, notably those comprising a heterocyclic vinyl monomer such as polyvinylpyrrolidone/$H_2O_2$ complexes, in particular in powder form; oxidases that produce hydrogen peroxide in the presence of a suitable substrate (for example glucose in the case of glucose oxidase or uric acid with uricase).

Preferably, the chemical oxidizing agent(s) are chosen from hydrogen peroxide, urea peroxide, alkali metal bromates or ferricyanides, peroxygenated salts, and mixtures of these compounds.

Particularly preferably, the chemical oxidizing agent is hydrogen peroxide.

Preferably, the chemical oxidizing agent(s) represent from 0.05% to 40% by weight, preferably from 0.5% to 30% by weight, more preferentially from 1% to 20% by weight and better still from 1.5% to 15% by weight relative to the total weight of the oxidizing composition (B).

Preferably, the oxidizing composition (B) according to the invention does not contain any peroxygenated salts.

As indicated previously, according to one embodiment of the invention, the oxidizing composition (B) comprises one or more scleroglucan gums, preferably in a total content of greater than or equal to 0.5% by weight relative to the weight of the composition.

Preferably, according to this embodiment, the scleroglucan gum(s) that may be used according to the invention preferably represent from 0.5% to 10% by weight, more preferentially from 0.5% to 5% by weight, even more preferentially from 0.5% to 3% by weight, even more preferentially and even more preferentially from 0.7% to 2% by weight relative to the total weight of the oxidizing composition (B).

The oxidizing composition (B) may also contain various additional compounds or various adjuvants conventionally used in compositions for dyeing the hair and notably as defined previously.

The oxidizing composition (B) is generally an aqueous composition. For the purposes of the invention, the term "aqueous composition" means a composition comprising more than 20% by weight of water, preferably more than 30% by weight of water and even more advantageously more than 40% by weight of water.

Preferably, the oxidizing composition (B) usually comprises water, which generally represents from 10% to 98% by weight, preferably from 20% to 96% by weight, preferably from 50% to 95% by weight, relative to the total weight of the composition.

This oxidizing composition (B) may also comprise one or more water-soluble organic solvents as described previously. It may also comprise one or more acidifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Usually, the pH of composition (B) is less than 7.

The pH of composition (B) of the invention is advantageously between 1 and 7, preferably between 1 and 4 and more preferentially from 1.5 to 3.5.

Finally, the oxidizing composition (B) is in various forms, for instance a solution, an emulsion or a gel.

Dyeing Process

The process of the invention may be performed by applying the dye composition (A) as defined previously and the oxidizing composition (B) successively and without intermediate rinsing, the order being irrelevant.

According to another preferred variant, a ready-to-use composition obtained by extemporaneous mixing, at the time of use, of the dye composition (A) as defined previously and of the oxidizing composition (B) is applied to wet or dry keratin fibers. According to this embodiment, preferably, the weight ratio R of the amounts of (A)/(B) ranges from 0.1 to 10, preferably from 0.2 to 2 and better still from 0.3 to 1.

In addition, independently of the variant used, the application of the ready-to-use composition to the keratin materials (resulting either from the extemporaneous mixing of the dye composition (A) and the oxidizing composition (B) or from the partial or total successive application thereof) is left in place for a time generally from about 1 minute to 1 hour and preferably from 5 minutes to 30 minutes.

The temperature during the process is conventionally between room temperature (between 15 and 25° C.) and 80° C. and preferably between room temperature and 60° C.

After the treatment, the keratin materials are optionally rinsed with water, optionally subjected to washing followed by rinsing with water, and are then dried or left to dry.

Preferably, the keratin fibers are human keratin fibers, preferably human hair.

A subject of the invention is also a ready-to-use composition for dyeing keratin fibers, in particular human keratin fibers such as the hair, obtained by extemporaneous mixing, at the time of use, of a composition (A) comprising:
  one or more oxidation dyes;
  one or more scleroglucan gums in a total amount of greater than or equal to 0.5% by weight relative to the weight of the composition;
  one or more mineral alkaline agents; and
  one or more organic alkaline agents chosen from alkanolamine(s);
  and a composition (B) comprising
  one or more chemical oxidizing agents.

The term "extemporaneous" notably means less than 30 minutes, preferably less than 15 minutes, before application to the keratin fibers, preferably less than 5 minutes. In particular, the mixture is applied immediately after having been prepared.

According to a particular embodiment of the invention, the chemical oxidizing agent(s) preferably represent a total content ranging from 0.1% to 20% by weight, preferably from 0.5% to 15% by weight or even more preferentially from 1% to 10% by weight, relative to the total weight of the ready-to-use composition.

Finally, the invention relates to a multi-compartment device comprising, in a first compartment, a dye composition (A) as described previously, and, in a second, an oxidizing composition (B) comprising one or more oxidizing agents, these compositions having been described previously.

In particular, a subject of the invention is also a multi-compartment device (or "kit") allowing the implementation of the composition for dyeing keratin fibers, preferably comprising at least two compartments, a first compartment containing the dye composition (A) as defined previously, and the second compartment containing at least one oxidizing composition (B) comprising at least one chemical oxidizing agent, preferably chosen from hydrogen peroxide and/or one or more systems for generating hydrogen peroxide, preferably hydrogen peroxide, the compositions in the compartments being intended to be mixed before application, to give the formulation after mixing; in particular, the kit may be an aerosol device.

The examples that follow serve to illustrate the invention without, however, being limiting in nature.

In particular, the dyeing of the keratin fibers obtained in these examples may advantageously be evaluated in the CIE $L^*$ $a^*$ $b^*$ system, using a Datacolor Spectraflash SF600X spectrocolorimeter.

In this $L^*$ $a^*$ $b^*$ system, the three parameters respectively denote the intensity of the color ($L^*$), the green/red color axis ($a^*$) and the blue/yellow color axis ($b^*$). The higher the value of $L^*$, the lighter the color. The higher the value of $a^*$, the redder the color and the higher the value of $b^*$, the yellower the color.

The variation (or extent) of the dyeing between untreated locks of hair and locks of hair after treatment is defined by the parameter DE* and is calculated according to the following equation:

$$DE^* = \sqrt{(L^*-L_o^*)^2 + (a^*-a_o^*)^2 + (b^*-b_o^*)^2} \quad (I)$$

In this equation, the parameters $L^*$, $a^*$ and $b^*$ represent the values measured on locks of hair after dyeing and the parameters $L_o^*$, $a_o^*$ and $b_o^*$ represent the values measured on untreated locks of hair. The higher the value of DE*, the better the dyeing of the keratin fibers.

In the CIE $L^*$, $a^*$, $b^*$ system, the chromaticity is calculated according to the following equation:

$$C^* = \sqrt{a^{*2} + b^{*2}}$$

The higher the value of $C^*$, the more chromatic the coloring.

EXAMPLE 1

The following compositions were prepared from the following ingredients in the following proportions indicated in grams of active substance:

| | Comparative composition C1 not according to the invention | Comparative composition C2 not according to the invention | Comparative composition C3 not according to the invention | Composition A1 (according to the invention) |
|---|---|---|---|---|
| Ammonium hydroxide | 2.47 | 2.47 | 2.47 | 2.47 |
| Ethanolamine | 4 | 4 | 4 | 4 |
| EDTA | 0.2 | 0.2 | 0.2 | 0.2 |
| Sodium sulfite | 0.5 | 0.5 | 0.5 | 0.5 |
| Oxidation dyes | 1.401 | 1.401 | 1.401 | 1.401 |
| Fragance | qs | qs | qs | qs |
| Hexadimethrine chloride | 0.3 | 0.3 | 0.3 | 0.3 |
| Polyquaternium-6 | 0.4 | 0.4 | 0.4 | 0.4 |
| Cetylhydroxyethyl cellulose | 0.2 | 0.2 | 0.2 | 0.2 |
| Xanthan gum | 1 | — | — | — |
| Algin | — | — | 1 | — |
| Sclerotium gum | — | — | — | 1 |
| Hydroxypropylcellulose | — | 1 | — | — |
| Water | qs 100 | qs 100 | qs 100 | qs 100 |
| Glycerol | 10 | 10 | 10 | 10 |
| Cetrimonium chloride | 0.25 | 0.25 | 0.25 | 0.25 |
| Caprylyl/capryl glucoside | 0.6 | 0.6 | 0.6 | 0.6 |
| Ascorbic acid | 0.4 | 0.4 | 0.4 | 0.4 |

Visual Evaluation of the Stability of the Compositions

The stability of the dye compositions was evaluated by observing the compositions at T0 (immediately after preparation of the composition) and then after 2 months of storage at 45° C.

| | Composition C1 | Composition C2 | Composition C3 | Composition A1 |
|---|---|---|---|---|
| Observation at T0 at room temperature (25° C.) | Liquid texture Non-homogeneous (phase separation) | Liquid texture Non-homogeneous (phase separation) | Liquid texture Non-homogeneous (phase separation) | Translucent gel Homogeneous (no phase separation) |
| Observation after 2 months at 45° C. | Liquid texture Non-homogeneous (phase separation) | Liquid texture Non-homogeneous (phase separation) | Liquid texture Non-homogeneous (phase separation) | Translucent gel Homogeneous (no phase separation) |

It is observed that composition A1 according to the invention is homogeneous and forms a translucent gel at T0. After 2 months at 45° C., composition A1 according to the invention is stable; it is homogeneous and translucent. Comparative compositions C1, C2 and C3 in which the scleroglucan gum has been replaced weight-for-weight with another thickener of polysaccharide type are not stable. Indeed, they are not homogeneous; phase separation of these compositions is observed as early as T0.

EXAMPLE 2

The following compositions were prepared from the following ingredients in the following proportions indicated in grams:

|  | Composition A2 according to the invention | Comparative Composition C4 not according to the invention |
|---|---|---|
| Ammonium hydroxide | 2.47 | 2.47 |
| Ethanolamine | 4.47 | 4.47 |
| EDTA | 0.2 | 0.2 |
| Sodium Sulfite | 0.5 | 0.5 |
| TOLUENE-2,5-DIAMINE | 0.4 | 0.4 |
| 2-METHYL-5-HYDROXYETHYLAMINOPHENOL | 0.264 | 0.264 |
| 4-AMINO-2-HYDROXYTOLUENE | 1.304 | 1.304 |
| HYDROXYETHOXY AMINOPYRAZOLOPYRIDINE HCL | 1.76 | 1.76 |
| p-Aminophenol | 0.128 | 0.128 |
| Fragance | qs | qs |
| Cetylhydroxyethylcellulose | 0.2 | 0.4 |
| Sclerotium gum | 0.6 | 0.4 |
| Water | Qs 100 | qs 100 |
| Glycerol | 10 | 10 |
| Cocoyl betaine | 0.15 | 0.15 |
| Caprylyl/capryl glucoside | 0.6 | 0.6 |
| Ascorbic acid | 0.4 | 0.4 |

Visual Evaluation of the Stability of the Compositions

The stability of the dye compositions was evaluated by observing the compositions at T0 (immediately after preparation of the composition), then after 2 months of storage at room temperature (25° C.), and after 2 months of storage at 45° C.

|  | Composition A2 according to the invention | Comparative composition C4 |
|---|---|---|
| Observation at T0 (immediately after preparation) | Homogeneous (no phase separation) Texture: smooth gel | Homogeneous (no phase separation) Texture: smooth gel |
| Observation after 2 months at 25° C. | Homogeneous (no phase separation) Texture: smooth gel | Phase separation: gel with presence of a liquid release |
| Observation after 2 months at 45° C. | Texture: smooth gel Homogeneous (no phase separation) | Phase separation: gel with presence of a liquid release |

It is observed that composition A2 according to the invention which comprises a content of scleroglucan gum of greater than or equal to 0.5 by weight relative to the total weight of the composition is stable at room temperature and at 45° C. for 2 months, unlike the comparative composition C4 which comprises a content of scleroglucan gum of 0.4% by weight relative to the weight of the composition. Compositions A2 and C4 comprise the same total content of thickener(s) (0.8%). Comparative composition C4 is therefore not stable.

EXAMPLE 3

The following composition according to the invention was prepared from the following ingredients in the following proportions indicated in grams:

| US INCI | Composition A3 According to the invention |
|---|---|
| AMMONIUM HYDROXIDE | 2.47 |
| ETHANOLAMINE | 4.73 |
| EDTA | 0.2 |
| SODIUM SULFITE | 0.5 |
| TOLUENE-2,5-DIAMINE | 0.16 |
| 4-AMINO-2-HYDROXYTOLUENE | 0.92 |
| 5-AMINO-6-CHLORO-o-CRESOL | 0.2 |
| 1-HYDROXYETHYL 4,5-DIAMINO PYRAZOLE SULFATE | 1.44 |
| p-AMINOPHENOL | 0.12 |
| FRAGRANCE | qs |
| CETYL HYDROXYETHYLCELLULOSE | 0.2 |
| SCLEROTIUM GUM | 1 |
| WATER | QS 100 |
| GLYCERIN | 10 |
| COCO-BETAINE | 0.15 |
| CETRIMONIUM CHLORIDE |  |
| CAPRYLYL/CAPRYL GLUCOSIDE | 0.6 |
| ASCORBIC ACID | 0.4 |

Visual Evaluation of the Stability of the Compositions

The stability of the dye composition was evaluated by observing the composition at T0 (immediately after preparation of the composition), then after 2 months of storage at room temperature (25° C.), and after 2 months of storage at 45° C.

|  | Composition A3 according to the invention |
|---|---|
| Observation at T0 (immediately after preparation) | Homogeneous (no phase separation) Texture: smooth gel |
| Observation after 2 months at 25° C. | Homogeneous (no phase separation) Texture: smooth gel |
| Observation after 2 months at 45° C. | Homogeneous (no phase separation) Texture: smooth gel |

It is observed that the composition according to the invention is translucent and stable at room temperature and at 45° C. for 2 months.

Composition A3 was mixed with 1 times its weight of 20-volumes oxidizing agent (6 g % of H2O2 AM); the mixture thus obtained was applied to locks of natural hair containing 90% white hairs.

The "mixture/lock" bath ratio is, respectively, 10/1 (g/g).

The leave-on time is 30 minutes, on a hotplate set at 27° C. On conclusion of the leave-on time, the locks are rinsed and then dried under a drying hood at 40° C.

The color of the locks was evaluated in the CIE L* a* b* system, using a Datacolor Spectraflash SF600X sectrocolorimeter.

|  | L* |
|---|---|
| Coloring obtained with the mixture of composition A3 + oxidizing agent (according to the invention) | 28.03 |

Composition A3 according to the invention allows an intense coloring of the keratin fibers to be obtained.

EXAMPLE 4

The following composition was prepared from the following ingredients in the following proportions indicated in grams:

|  | Composition A4 according to the invention |
|---|---|
| Ammonium hydroxide | 1.23 |
| Arginine | 3 |
| Ethanolamine | 5 |
| EDTA | 0.2 |
| Sodium Sulfite | 0.5 |
| Citric acid | 3.3 |
| Sodium metasilicate | 2 |
| Toluene-2,5-diamine | 0.16 |
| 4-amino-2-hydroxytoluene | 0.92 |
| 5-Amino-6-chloro-o-cresol | 0.2 |
| 1-Hydroxyethyl 4,5-diaminopyrazole sulfate | 1.44 |
| p-Aminophenol | 0.12 |
| Fragance | qs |
| Polyquaternium-11 | 1.84 |
| Hexadimethrine chloride | 1.2 |
| Polyquaternium-6 | 0.8 |
| Cetylhydroxyethylcellulose | 0.2 |
| Sclerotium gum | 1 |
| Water | Qs 100 |
| Glycerol | 10 |
| Cetrimonium chloride | 0.25 |
| Caprylyl/capryl glucoside | 0.6 |
| Ascorbic acid | 0.4 |

Visual Evaluation of the Stability of the Compositions

The stability of the dye composition was evaluated by observing it at T0, then after 48 hours at room temperature (25° C.), and then after 2 months of storage at 45° C.

|  | Composition A4 |
|---|---|
| Observation at T0 (immediately after preparation) at room temperature (25° C.) | Translucent gel Homogeneous (no phase separation) |
| Observation after 2 months at 45° C. | Translucent gel Homogeneous (no phase separation) |

It is observed that composition A4 according to the invention is homogeneous and forms a translucent gel at T0. After 2 months at 45° C., composition A4 according to the invention is stable and in the form of a homogeneous and translucent gel.

Composition A4 was mixed with 1 times its weight of 20-volumes oxidizing agent (6 g % of $H_2O_2$ AM). The mixture thus obtained was applied to locks of natural hair containing 90% white hairs.

The "mixture/lock" bath ratio is, respectively, 10/1 (g/g).

The leave-on time is 30 minutes, on a hotplate set at 27° C. On conclusion of the leave-on time, the locks are rinsed and then dried under a drying hood at 40° C.

The color of the locks was evaluated in the CIE L* a* b* system, using a Datacolor Spectraflash SF600X spectrocolorimeter.

An intense coloring (L*=24.95) of the keratin fibers is obtained.

The invention claimed is:

1. A composition for dyeing keratin fibers, comprising:
   at least one oxidation dye;
   at least one scleroglucan gum present in a total amount of greater than or equal to 0.5% by weight, relative to the total weight of the composition;
   at least one mineral alkaline agent; and
   at least one organic alkaline agent chosen from alkanolamines.

2. The composition of claim 1, wherein the at least one scleroglucan gum is present in an amount ranging from 0.5% to 10% by weight, relative to the total weight of the composition.

3. The composition of claim 1, wherein the at least one oxidation dye is chosen from benzene-based oxidation bases, or salts thereof, optionally combined with at least one coupler chosen from meta-phenylenediamines, meta-aminophenols, meta-diphenols, naphthalene-based couplers, heterocyclic couplers, or salts thereof.

4. The composition of claim 1, wherein the at least one oxidation dye is chosen from para-phenylenediamines, bis(phenyl)alkylenediamines, para-aminophenols, ortho-aminophenols, heterocyclic bases, or salts thereof.

5. The composition of claim 1, wherein the at least one mineral alkaline agent is chosen from aqueous ammonia, ammonia precursors, alkali metal or alkaline-earth metal silicates, phosphates, carbonates, bicarbonates, sodium or potassium hydroxide, or mixtures thereof.

6. The composition of claim 1, wherein the at least one mineral alkaline agent is present in a total amount ranging from 0.1% to 10% by weight, relative to the total weight of the composition.

7. The composition of claim 1, wherein the alkanolamines are chosen from monoalkanolamines, dialkanolamines, trialkanolamines, or mixtures thereof, comprising one to three identical or different $C_1$ to $C_4$ hydroxyalkyl radicals.

8. The composition of claim 1, wherein the alkanolamines are chosen from monoethanolamine, diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane, or mixtures thereof.

9. The composition of claim 1, wherein the at least one organic alkaline agent chosen from alkanolamines is present in a total amount ranging from 0.5% to 10% by weight, relative to the total weight of the composition.

10. The composition of claim 1, wherein the at least one mineral alkaline agent is chosen from aqueous ammonia (ammonium hydroxide) and the at least one organic alkaline agent chosen from alkanolamines is chosen from monoethanolamine.

11. The composition of claim 1, further comprising at least one additional alkaline agent other than the at least one mineral alkaline agent and the at least one organic alkaline agent chosen from alkanolamines.

12. The composition of claim 11, wherein the at least one additional alkaline agent is chosen from basic amino acids comprising histidine, lysine, arginine, ornithine, and citrulline.

13. The composition of claim 1, further comprising at least one nonionic associative polymer chosen from celluloses modified with groups including at least one fatty chain.

14. The composition of claim 13, wherein the at least one nonionic associative polymer is chosen from hydroxyethylcelluloses modified with groups including at least one fatty chain chosen from an alkyl group, an arylalkyl group, an alkylaryl group, or a mixture thereof.

15. The composition of claim 1, further comprising at least one cationic polymer chosen from:
(1) dialkyldiallylammonium homopolymers; and/or
(2) cationic polymers that are constituted of repeating units corresponding to the formula (IV):

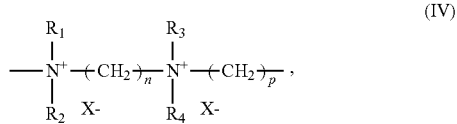

wherein in formula (IV), $R_1$, $R_2$, $R_3$, and $R_4$, which may be identical or different, are chosen from an alkyl or hydroxyalkyl radical containing from 1 to 4 carbon atoms, n and p are integers ranging from 2 to 20, and X— is an anion derived from a mineral or organic acid.

16. The composition of claim 1, further comprising at least one chemical oxidizing agent.

17. The composition of claim 16, wherein the at least one chemical oxidizing agent is chosen from hydrogen peroxide, or at least one system generating hydrogen peroxide.

18. A method for dyeing keratin fibers, comprising:
applying to the keratin fibers a dye composition (A) and an oxidizing composition (B);
wherein the dye composition (A) comprises:
at least one oxidation dye;
at least one scleroglucan gum present in a total amount of greater than or equal to 0.5% by weight, relative to the total weight of the dye composition (A);
at least one mineral alkaline agent; and
at least one organic alkaline agent chosen from alkanolamines; and
wherein the oxidizing composition (B) comprises at least one chemical oxidizing agent; and
wherein the oxidizing composition (B) is extemporaneously mixed with the dye composition (A) just before being applied to the keratin fibers, or alternatively, the dye composition (A) and the oxidizing composition (B) are applied sequentially to the keratin fibers without intermediate rinsing.

19. The method of claim 18, wherein the at least one chemical oxidizing agent is chosen from hydrogen peroxide and/or at least one system generating hydrogen peroxide.

20. A multi-compartment kit comprising:
a first compartment containing a dye composition comprising:
at least one oxidation dye;
at least one scleroglucan gum in a total amount of greater than or equal to 0.5% by weight, relative to the total weight of the dye composition;
at least one mineral alkaline agent; and
at least one organic alkaline agent chosen from alkanolamines; and
a second compartment containing at least one oxidizing composition comprising at least one chemical oxidizing agent.

* * * * *